US007030095B2

(12) United States Patent
Janssen et al.

(10) Patent No.: US 7,030,095 B2
(45) Date of Patent: Apr. 18, 2006

(54) PEDICULICIDAL AND OVACIDAL TREATMENT COMPOSITIONS AND METHODS FOR KILLING HEAD LICE AND THEIR EGGS

(75) Inventors: Herwig Janssen, Princeton, NJ (US); Kie Ho, Princeton, NJ (US); Glenn Nystrand, Lebanon, NJ (US); Dexter Williams, Dayton, NJ (US); C. Scott Lamb, Doylestown, PA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 68 days.

(21) Appl. No.: 10/230,460

(22) Filed: Aug. 29, 2002

(65) Prior Publication Data

US 2003/0087838 A1    May 8, 2003

Related U.S. Application Data

(62) Division of application No. 09/841,715, filed on Apr. 25, 2001.

(51) Int. Cl.
*A01N 43/22* (2006.01)

(52) U.S. Cl. .................. 514/28; 424/70.11; 424/78.02; 424/405; 424/406

(58) Field of Classification Search .................. 514/28; 424/405, 406, 70.11, 78.02, 70.1
See application file for complete search history.

(56) References Cited

U.S. PATENT DOCUMENTS

| | | | |
|---|---|---|---|
| 5,202,242 A | 4/1993 | Mynderse et al. | |
| 5,362,634 A | 11/1994 | Boeck et al. | |
| 5,496,931 A | 3/1996 | Boeck et al. | |
| 5,539,089 A | 7/1996 | Broughton et al. | |
| 5,571,901 A | 11/1996 | Boeck et al. | |
| 5,591,606 A | 1/1997 | Turner et al. | |
| 5,631,155 A | 5/1997 | Turner et al. | |
| 5,670,364 A | 9/1997 | Mynderse et al. | |
| 5,712,295 A | 1/1998 | Mencke et al. | |
| 5,767,253 A | 6/1998 | Turner et al. | |
| 5,817,608 A | 10/1998 | Bell | |
| 5,972,987 A | 10/1999 | Reid et al. | |
| 6,063,771 A | 5/2000 | Snyder | |
| 6,106,815 A * | 8/2000 | Kang et al. | 424/70.12 |
| 6,113,888 A | 9/2000 | Castro et al. | |
| 6,342,482 B1 | 1/2002 | Snyder | |

FOREIGN PATENT DOCUMENTS

| | | |
|---|---|---|
| EP | 0375316 | 6/1990 |
| EP | 0968706 | 1/2000 |
| EP | 0 607 642 B1 | 9/2000 |
| WO | 00/60940 | 10/2000 |
| WO | 01/11964 A1 | 2/2001 |
| WO | 0112156 | 2/2001 |

OTHER PUBLICATIONS

Mascarenhas, VJ, et al., Dosage-Mortality Responses of Third Instars of Beet Armyworm (Lepidoptera:Noctuidae) to Selected Insecticides, 15 Journal of Agricultural Entomology(2) Abstract (1998).

Crouse GD, Natural Products As Leads for New Pesticides with Reduced Risks, 215th American Chemical Society National Meeting, Abstract (1998).

Boyd, MI et al., Susceptibility of Predaceous Hemipteran Species to Selected Insecticides on Soybean in Louisiana, 91 Journal of Economic Entomology(2). Abstract (1998).

Kahn, I. et al., Citrus Thrips(Thysanoptera:Thripidae) Resistance Monitoring in California,91 Journal of Economic Entomology(2) Abstract (1998).

Mascarenhas, VJ et al., Suspectibility of Field Populations of Beet Armyworm (Lepidoptera:Noctuidae) to Commercialand Experimental Insecticides, 91 Journal of Economic Entomology(4) Abstract (1998).

Anzeveno,PB et al., Rhamnose Replacement Analogs of Spinosyn A., 216 American Chemical Society (1-3) Abstract (1998).

Salgado, VL, Studies on the Mode of Action of Spinosad: Insect Symptoms and PhysiologicalCorrelates, 60 Pesticide Biochemistry and Physiology (2) Abstract (1998).

Salgado, VL, et al., Studies on the Mode of Action of Spinosad: the Internal Effective Concentrationand the Concentration Dependenceof Neural Excitation, 60 Pesticide Biochemistryand Physiology (2) Abstract (1998).

Marty, MS, et al., The Maternaland Developmental Toxicity of Spinosad in Sprague-Dawley Rats and New Zealand White Rabbits,57 Teratology(4-5) Abstract (1998).

Creemer, LC et al., Conversion of Spinosyn A and Spinosyn D to Their Respective9- and 17-Pseudoaglycones and Their Aglycones,51/8 Journal of Antibiotics (Japan) Abstracts (1998).

Paquette, LA, Total Synthesis of Spinosyn A. 1. Enantioselective Constructions of a Key Tricyclic Intermediate by a Multiple Configurational Inversion Scheme, 120/11 Journal of the American Chemical Society, Abstract (1998).

Paquette, LA, Total Synthesis of Spinosyn A. 2. Degradation Studies Involving the Pure Factor and its Complete Reconstitution, 120/11 Journal of the American Chemical Society Abstract (1998).

(Continued)

*Primary Examiner*—Neil S. Levy
(74) *Attorney, Agent, or Firm*—Reed Smith, LLP

(57) ABSTRACT

The present invention relates to composition and methods for administering compositions in solutions for killing adult lice and the ova comprising water, PVM/MA Decadiene crosspolymers, propylene glycol, a mixture of cetyl and stearyl alcohols, Ceteareth-20; stearalkonium chloride; benzyl alcohol; hexylene glycol; pentylene glycol, isopropyl alcohol; a mixture of spinosyn A and spinosyn D in a weight ratio of 80:20, BHT; and sodium hydroxide.

12 Claims, No Drawings

OTHER PUBLICATIONS

Trial with Biological Meterials to Control Chaetanaphothrips Orchidii in Biological Cirtus Orchard—Ga'aton 1997, 52 Alon Hanotea, Abstract (1998).

Secher, B.J.M, Adjusting Dosages According to Canopy Densities—a New Concept for Dosing Fungicides and Insecticides 15th Danish Plant Protection Conferences. Pests and Diseases,3 DJF Rapport, pp. 145-150, Abstract (1998).

Kirst, H.A., Fermentation-Derived Compounds as a Source of New Products, 70 Pure and Applied Chemistry Abstract (1998).

New Products (pesticides) (3 tables), Chemical Business Newsbase (Informatore Fitopatologico) Abstract Oct. 13, 1998.

Several Pesticide Petitions filed, Chemical Business Newsbase (Federal Register) Abstract Oct. 12, 1998.

Notice of Filing of Pesticide Petitions, Chemical Business Newsbase (Federal Register), Abstract Sep. 23, 1998.

EPA Issues Exemptions for Inert Ingredient Source, Fungicide; Time-Limited Tolerance for Spinosad, Tolerances for Triasulfuron Issued, Chemical Business Newsbase (Pesticide And Toxic Chemical News), Abstract Sep. 11, 1998.

EPA Issues Tolerance Exemption, Proposes Time-Limited Tolerance, Chemical Business Newsbase (Pesticide and Toxic Chemical News), Abstract Aug. 21, 1998.

Spinosad: Pesticide Tolerance, Chemical Business Newsbase (Federal Register), Abstract Aug. 18, 1998.

Spinosad; Time-Limited Pesticide Tolerance, Chemical Business Newsbase (Federal Register), Abstract Aug. 4, 1998.

Strategic Diagnostics Inc. and Dow AgroSciences Immunoassay Method for Spinosad is First EPA Method Suitable for Tolerance Enforcement,8:22 Business Wire, Abstract May 28, 1998.

Natural Organisms Provide Leads for Developing New Pesticides, Chemical Business Newsbase (Pesticide and Toxic Chemical News), Abstract May 12, 1998.

EnvironmentalProtection Agency 40 CFR Part 180 (OPP-300644;FRL-5785-7); Chemical Business Newsbase (Federal Register) Summary, Apr. 21, 1998.

Crouse, GD et al., Naturally Derived Materials as Products and Leads for Insect Control: The Spinosyns, Pesticides and the Future: Minimizing Exposure of Humans and the Environment, Reviews in Toxicology (2) Abstract (1998).

Coscolla, R, et al, Essai sur l'efficacite du "Spinosad" dans la lutte contre la torteuse de la grappe (Lobesia botrana), IOBC WPRS Bulletin, 1998, vol. 21, No. 2 Abstract.

Spinosad; Pesticide.Tolerance, Fed. Registr. 63 (157), 43629-43637 Abstract (1998).

Crouse, GD, et al., Naturally Derived Materials as Products and Leads for Insect Control: the Spinosyns, Rev. Toxicol. (2) Abstract (1998).

Racke, KD, Pesticides for Turfgrass Pest Management: Uses and Environmental Issues, Book of Abstracts, 216th ACS National Meeting, Abstract (1998).

Salgado, VL, Studies on the Mode of Action of Spinosad: Insect Symptoms and Physiological Correlates, Pestic. Biochem. Physiol(2). Abstract (1998).

Obando-Rodriguez,A. et al., Confirm 2F and Tracer as an Useful Alternative for Integrated Pest Management (IMF) Against Bollworm, Tobacco Budworm and Beet Armyworm in Cotton in Northern Mexico, 2 Proc.—Beltwide Cotton Conf. Abstract (1998).

Roberts, P., BT Cotton: Impact of Supplemental Sprays, 2 Proc.—Beltwide Cotton Conf. Abstract (1998).

Peterson, IG, The Ovicidal Activity of Tracer Naturalyte Insecticide Against Heliothine Species in Conventional Cotton, 2 Proc.—Beltwide Cotton Conf. Abstract (1998).

Herbert, DA, Evaluation of Thrips Damage on Maturity and Yield of Virginia Cotton, 2 Proc.—Beltwide Cotton Conf. Abstract (1998).

Duffie, WD et al, Predator Mortality in Cotton From Different Insecticide Classes, 2 Proc.—Beltwide Cotton Conf. Abstract (1998).

Pacheco, JL, A Five Year Review of Lygus Efficacy and Cotton Yield Studies in Central Arizona, 2 Proc. Beltwide Cotton Conf. Abstract (1998).

Environmental Protection Agency, Spinosad; Pesticide Tolerances, Fed. Registr.63 (72), 18329-18338 Abstract (1998).

Yee, W.L. et al., Laboratory Evaluationsof Synthetic and Natural Insecticides on Beet Armyworm (Lepidoptera: Noctuidae) Damage and Survival on Lettuce, 91 J. Econ. Entomol. (1) Abstract (1998).

"Head Lice" Yahoo! Health, http://health.yahoo.com/health/diseases_and_conditions/disease_feed_data/head_lice_/ Nov. 5, 1999.

"What You Should Know About . . . Head Lice in the Child Care Setting" http://www.cdc.gov/pcidod/hip/abc/facts18.htm Nov. 5, 1999.

International Cosmetic Ingredient Dictionary and Handbook, 8th ed., 2000, vol. 2, p. 1727, 1752-1755, 1757-1759, 1764-1765 1768-1782, 1789-1804, 1808, and 1810-1812.

* cited by examiner

PEDICULICIDAL AND OVACIDAL TREATMENT COMPOSITIONS AND METHODS FOR KILLING HEAD LICE AND THEIR EGGS

CROSS-REFERENCES TO RELATED APPLICATIONS

This application is a divisional of U.S. Ser. No. 09/841,715, filed Apr. 25, 2001.

FIELD OF THE INVENTION

The present invention relates to compositions and methods for controlling and treating adult lice and nits (or ova) of species of the order of Anoplura, including but not limited to pediculus capitis, pediculus humanus and pthiris pubic, by applying a composition of pediculicides and ovacides in solution to skin and hair, including but not limited to human skin and hair. The compositions comprise effective pediculicidal agents and ovacidal agents which are solubilized to promote penetration of the ova. More particularly, the effective pediculicidal agents and ovacidal agents are spinosad, Spinosyn A, Spinosyn D, or combinations thereof.

BACKGROUND OF THE INVENTION

Lice present a source of serious health problems worldwide for man and animals. Not only do lice carry a variety of bacteria on their outer surfaces, but in their fecal matter as well. Lice transmit the bacteria to their hosts through puncture wounds which are inflicted during feeding, since lice must feed from their host's blood. Ailments ranging from skin infections to typhus can be traced back to lice infestation.

Lice belong to the order Anoplura. Specific species that affect human beings include *pediculus capitis* (head lice), *pediculus humanus* (body lice) and *pthiris pubic* (pubic lice). Lice are capable of spreading rapidly. A fertilized female lays about six to eight eggs, or nits, every twenty-four hours. It has been estimated that a single female louse and her daughters could have 112,778 offspring in a period of forty-eight days.

Pediculus capitis clings to the hair shaft when feeding, mating, and laying eggs. Removal of nits is particularly difficult, as each nit is cemented to a shaft of hair by a glycoprotein glue, acting as a binding cement. Lice eggs themselves are covered by a chitinous sheath which surrounds both the nit and the attached hair shaft.

Various methods and compositions have been used to remove lice, for example mechanical removal with combs and chemical removal with insecticides (known as pediculicides). Pediculicides, such as lindane and various permethrins, have been used in conjunction with shampoos for killing and rinsing out lice. However, as noted in the prior art, the use of these methods and compositions is not entirely effective in controlling head lice, as some lice often survive the treatment. Indeed, the National Pediculosis Association has reported that twenty to eighty percent of nits survive initial pediculicide treatment, resulting in reinfestation.

In the prior art, pyrethrum, permethrin, and lindane pesticides, all work as central nervous system toxins on lice. Their effectiveness depends on their ability to reach the functioning central nervous system on lice. Unfortunately, nits do not develop a functioning central nervous system until they are between three and four days old, during an average incubation period of approximately ten days. As a result, only sixty to seventy percent of nits treated can be killed upon application of one of these pediculicides.

Moreover, recently, lice may have begun to develop resistance to current pediculicides. For example, resistance has already been documented in Europe, United States and Israel. Thus, a new active to kill lice and their eggs is desirable.

It has been discovered that Spinosyn A and Spinosyn D, compounds that have been used as insecticides for turf building and ornamental plants may be used for killing lice. Spinosyn A and Spinosyn D are components of a fermentation product derived from the bacterium species *Saccharopolyspora spinosa*. The bacteria decomposes much of the organic matter in soil and the most active metabolites from this fermentation were identified as Spinosyn A and D.

The chemical structure of spinosad contains two sugar molecules, one located at each end. A tetracyclic ring structure joins the two sugars. This structure is one of a class of compounds called macrolides. The chemical structure of spinosyns has the general formula of:

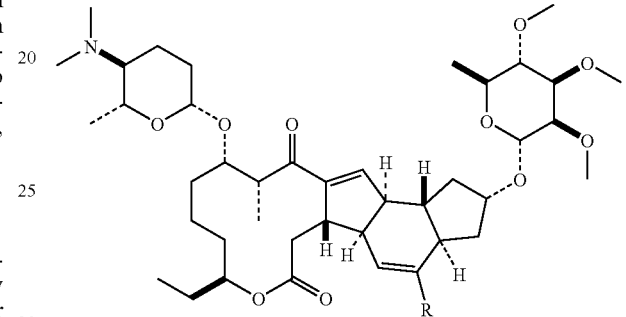

R is defined as any chemical group which provides pediculicidal and ovacidal properties, most preferably H and CH3.

It is known that Spinosyn A and Spinosyn D are useful as insecticides against *Lepidoptera* and *Diptera* species. Spinosyns have been used in a pediculicidal shampoo. The prior art does not teach the use of spinosyns in solution.

Known pediculicides have been noted to be ineffective on killing ova. Thus, the use of these pediculicides results in a reinfestation of the hair or skin as soon as the ova hatch, since the treatment was ineffective in controlling and killing the ova. A need has arisen to develop an effective treatment for both adult lice and their ova in a cosmetically elegant form.

SUMMARY OF THE INVENTION

The present invention includes a composition comprising an effective amount of one or more agents having pediculicidal and ovacidal properties for adult lice and nits of a specie of order Anoplura in solution.

Another embodiment of the invention comprises pediculicidal agents and ovacidal agents in solution for adult lice and nits which comprise the chemical structure of:

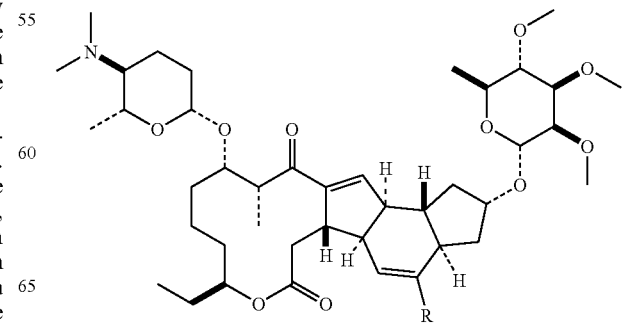

In another embodiment, the present invention includes a composition comprising a mixture of spinosyn A and spinosyn D in an approximate weight ratio of 85:15, water, methyl vinyl ether/maleic anhydride crosslinked with 1,9 decadiene, propylene glycol, a mixture of cetyl and stearyl alcohols, ceteareth-20, stearalkonium chloride, benzyl alcohol, pentylene glycol, isopropyl alcohol, BHT and sodium hydroxide.

The present invention includes a method of controlling adults and ova of the species of order Anoplura by topically applying to one or more of skin and hair a composition comprising an effective amount of one or more agents having pediculicidal and ovacidal properties for adult lice and nits of a specie of order Anoplura in solution. The pediculicidal and ovacidal properties include the abilities to control adult lice and lice ova (or nits).

The present invention includes a method of controlling adults and ova of the species of order Anoplura by topically applying to one or more of skin and hair a composition comprising an effective amount of one or more agents having pediculicidal and ovacidal properties for adult lice and nits of a specie of order Anoplura in solution, which agents comprise the chemical structure of:

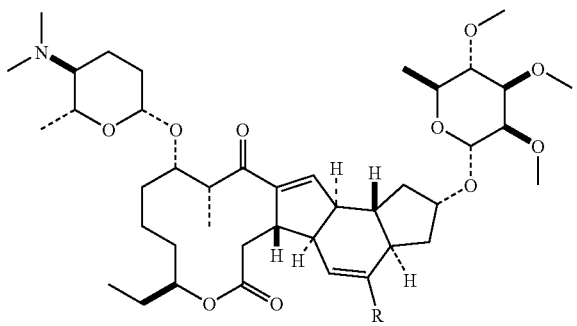

The present invention includes a method of controlling adults and ova of the species of order Anoplura by topically applying to one or more of skin and hair a composition comprising a mixture of spinosyn A and spinosyn D in an approximate weight ratio of 80:20, water, methyl vinyl ether/maleic anhydride crosslinked with 1,9 decadiene, propylene glycol, a mixture of cetyl and stearyl alcohols, ceteareth-20, stearalkonium chloride, benzyl alcohol, pentylene glycol, isopropyl alcohol, BHT and sodium hydroxide.

Another embodiment of the present invention includes a method of controlling adults and ova of the species of order Anoplura by topically applying to one or more of skin and hair a composition comprising about 1 to about 2.2% of Spinosyn A & D in an approximate weight ratio of 85:15, about 44% deionized water, about 1.1 Stabileze QM, about 3% propylene glycol, about 3% cetostearyl alcohol NF, about 0.9% Ceteareth-20, about 4.17% stearalkonium chloride (or Ammonyx 4 (18%)), about 10% benzyl alcohol, about 6% hexylene glycol, about 4% pentylene glycol, about 20% isoproyl alcohol, about 0.1% BHT and about 1.2 to about 1.9% sodium hydroxide (10% solution).

A further separate embodiment of the present invention is a method for solubilizing agents having pediculicidal and ovacidal properties comprising combining one or more solvents and an effective amount of one or more agents having pediculicidal and ovacidal properties; wherein the agents comprise a chemical structure of:

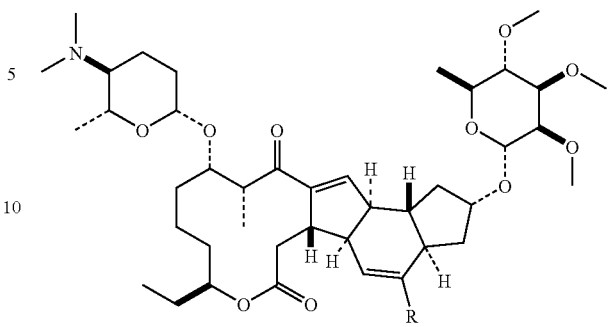

DETAILED DESCRIPTION OF THE INVENTION

The present invention relates to a composition comprising an effective amount of agents with pediculicidal and ovacidal properties in a cosmetically elegant solution or emulsion, including but not limited to imidacloprid, spinosad, a spinosyn, Spinosyn A, Spinosyn D, any component produced from the *Saccharopolyspora spinosa* species or combinations. Additionally, the present invention includes the method of applying a pediculicide and ovacide composition in solution to hair or skin for the control of adults and nits of a specie of the order Anoplura.

Spinosyn A and Spinosyn D are also known as A83543A and A83543D respectively. Both Spinosyn A and Spinosyn D are the major components of a fermentation product known as A83543. This fermentation product, A83543, is produced by the species *Saccharopolyspora spinosa*.

What is meant by "an effective amount" refers to an amount of imidacloprid, spinosad, spinosyn, Spinosyn A, Spinosyn D or a combination thereof sufficient to decrease the number of live lice and viable nits, i.e. eggs. The effective amount can typically range from greater than about 0% to about 10%, preferably, about 0.5% to about 5%. (All percentages in this disclosure are weight percentages.)

When "effective amount" refers to solvents, solubilizing agents or solutions, the term means that the solvents solubilize the pediculicidal agents and ovacidal agents and also that the solution has a concentration that effectively controls the lice and ova.

What is meant by "skin" refers to that of an animal, preferably a mammal, most preferably a human. Skin that would be commonly prone to nits includes that of the scalp, body, and pubis areas.

What is meant by "to control" is to reduce the number of viable nits and live lice. The extent of reduction accomplished by the composition depends upon the application rate of the composition, the choice of imidacloprid, spinosad, spinosyn, Spinosyn A, Spinosyn D, any component produced from the *Saccharopolyspora spinosa* species and a combination thereof, and the species of Anoplura targeted.

The order Anoplura includes the following families: echniophtiriidae, enderleinellidae, haematopinidae, linognathidae, pecaroecidae, pediculidae, polyplacidae, and pthiridae. Examples of species in the order Anoplura include, but are not limited to pediculus humanus, pediculus capitis, and pthiris pubis. These three species are known more commonly as the body louse, head louse, and pubic louse.

What is meant by "solubilizing agent" or "solvent" refers to solvents capable of solubilizing the pediculicides and ovacides, preferably in the minimum amount required to solubilize the pediculicides and ovacides, preferably about 3% propylene glycol, about 10% benzyl alcohol, about 6% hexylene glycol, about 4% pentylene glycol, and about 20% isopropyl alcohol. Examples of solubilizing agents include, but are not limited to, glycols, for example, propylene glycol, polyethylene glycol, dipropylene glycol, pentylene glycol, and methoxypolyethylene glycol, hexylene glycol, butylene glycol; benzyl alcohol; isopropyl alcohol; preferably penetylene glycol; combinations of pentylene glycol, benzyl alcohol and isopropyl alcohol, either with or without one of the following: hexylene glycol, butylene glycol, dipropylene glycol, methoxypolyethylene glycol or propylene glycol; or combinations of hexylene glycol, butylene glycol, benzyl alcohol and isopropyl alcohol ("Solvent Matrices"). These Solvent Matrices are capable of solubilizing poorly soluble drugs, including but not limited to imidacloprid, spinosad, spinosyn, spinosyn A, spinosyn D, any component produced by the *Saccharopolyspora spinosa* species and a combination thereof. These Solvent Matrices have the additional function of aiding in the penetration of the ova of the louse.

The compositions of this invention comprise an effective amount of pediculicidal agents and ovacidal agents in solution, used for controlling lice and its ova. The solvents are beneficial because they solubilize the pediculicidal agents and ovacidal agents, and also promote the penetration of the ova so that the ovacidal agents are highly effective. Without being bound by a mechanism, the present invention is believed to better penetrate lice and its ova. Additionally, the compositions of this invention are cosmetically elegant. The preferred solvents are benzyl alcohol, pentylene glycol, isopropyl alcohol, hexylene glycol, butylene glycol, dipropylene glycol and combinations thereof. More particularly, the pediculicidal agents and ovacidal agents may be, including but not limited to imidacloprid, spinosad, spinosyn, Spinosyn A, Spinosyn D, any component produced from the *Saccharopolyspora spinosa* species or a combination thereof. The preferred pediculicidal agent and ovacidal agent is a combination of Spinosyn A and Spinosyn D in a weight ratio of 85/15 or 80/20.

The compositions disclosed in this patent have an improved solubility of pediculicides and ovacides, including but not limited to imidacloprid, spinosad, spinosyn, Spinosyn A, Spinosyn D, any component produced from the *Saccharopolyspora spinosa* species or a combination thereof, which yields a more effective pediculicide and ovacide for the specie of the order of Anoplura. Specific species that affect human beings include *pediculus capitis* (head lice), *pediculus humanus* (body lice) and *pthiris pubic* (pubic lice).

More particularly, the pediculicides and ovacides are present in a composition with solvents and stabilizers. The solvents may help promote the penetration of the composition into the ova in order to act like a ovacide, in addition to being a pediculicide.

In one embodiment, the invention features a composition comprising an effective amount of one or more pediculicidal and ovacidal properties, which may include but is not limited to imidacloprid, spinosad, spinosyn, Spinosyn A, Spinosyn D, any component produced from the *Saccharopolyspora spinosa* species or a combination thereof; water; benzyl alcohol; hexylene glycol; pentylene glycol; butylene glycol; dipropylene glycol; isopropyl alcohol; and a non-acrylic stabilizer, for example, a co-polymer of methyl vinyl ether/maleic anhydride cross-linked with 1,9-decadiene. This composition is beneficial because it is capable of solubilizing the pediculicidal and/or ovacidal agents, which results in high mortality of adult lice and their ova.

In one embodiment, the solubilizing agents of the composition may include glycols, for example, propylene glycol, polyethylene glycol, dipropylene glycol, pentylene glycol, and methoxypolyethylene glycol, hexylene glycol, butylene glycol; benzyl alcohol; isopropyl alcohol; preferably penetylene glycol; combinations of pentylene glycol, benzyl alcohol and isopropyl alcohol, either with or without one of the following: hexylene glycol, butylene glycol, dipropylene glycol, methoxypolyethylene glycol or propylene glycol; or combinations of hexylene glycol, butylene glycol, benzyl alcohol and isopropyl alcohol.

The present invention also relates to a composition comprising an effective amount of one or more pediculicides and ovacides for nits and adult lice (collectively "Lice") of a specie of the order Anoplura and a solubilizing agent. The pediculicides and ovacides are ingredients which control the Lice, including but not limited to any component produced by the *Saccharopolyspora spinosa* species, imidacloprid (also known as NTN 33893, which is a proprietary chemical of Bayer AG), spinosad, spinosyn, Spinosyn A and Spinosyn D, and a combination thereof, preferably a mixture of Spinosyn A and Spinosyn D in an approximate weight ratio of 80:20. The preferable amount of stabilizers is between about 0.5 to about 1.5%.

What is meant by "cleansing surfactants" is one or more compounds used for skin and/or hair cleaning, and the cleansing surfactants are used in an amount which produces the desired function provided that the amount does not effect the stability of the solution. These compounds can also serve as cosmetic emulsifiers. Classes of compounds include soaps and fatty acids/alkali combinations. Examples include, but are not limited to, ammonium lauryl sulfate, ammonium laureth sulfate, sodium lauryl sulfate, sodium laureth sulfate. For a more complete listing of cleansing surfactants, herein incorporated by reference, see *CFTA Dictionary* 1789–1795.

What is meant by "emulsifying surfactants" is one or more compounds that reduce surface tension and the emulsifying surfactants are used in an amount which produces the desired function provided that the amount does not effect the stability of the solution. They create barriers around droplets to prevent them from coalescing. Emulsifiers could be, but are not limited to oil-in-water emulsifiers, water-in-oil emulsifiers, water-in-oil-in-water emulsifiers, oil-in-water-in-oil emulsifiers, silicone-in-water emulsifiers, and water-in-silicone emulsifiers. Examples include, but are not limited to, glyceryl trioleate, acetylated sucrose distearate, sorbitan trioleate, polyoxyethylene (1) monostearate, glycerol monooleate, sucrose distearate, polyethylene glycol (50) monostearate, octyl phenoxypoly (ethyleneoxy) ethanol, deacylerin penta-isostearate, sorbitan sesquioleate, hydroxylated lanolin, lanolin, triglyceryl diisostearate, polyoxyethylene (2) oleyl ether, calcium stearoyl-2-lactylate, cetearyl glucoside, methyl glucoside sesquistearate, sorbitan monopalmitate, methoxy polyethylene glycol-22/dodecyl glycol copolymer, polyethylene glycol-45/dodecyl glycol copolymer, polyethylene glycol 400 distearate and glyceryl stearate, cetyl phosphate, potassium cetyl phosphate. See also *CTFA Dictionary* 1796–1803.

What is meant by "foam-boosting surfactants" is one or more compounds that have the ability to either generate or stabilize foams and the foam-boosting surfactants are used in an amount which produces the desired function provided that the amount does not effect the stability of the solution. They generally increase the surface viscosity of the vehicle surrounding the bubbles. Examples of foam-boosting surfactants include, but are not limited to, cocamidoethyl betaine, cetyl betaine, disodium cetearyl sulfosuccinate, disodium oleoamphodipropionate, lauramide DEA, lauramidopropyl betaine. See also *CTFA Dictionary*, 1803–1804.

What is meant by "emollient skin conditioning agents" is one or more compounds that soften and smooth the skin and the emollient skin conditioning agents are used in an amount which produces the desired function provided that the amount does not effect the stability of the solution. These compounds achieve this effect lubricating the skin surface, encouraging skin water retention, and altering product textures. Examples include, but are not limited to, octyl hydroxystearate, lanolin, capric/caprylic triglyceride, cetyl palmitate, cetyl alcohol, isopropyl isostearate, glyceryl dilaurate, isopropyl myristate, palm alcohol, and sucrose cocoate. See also *CTFA Dictionary* 1768–1773.

What is meant by "humectants" is one or more compounds that prevent the skin from losing moisture and the humectants are used in an amount which produces the desired function provided that the amount does not effect the stability of the solution. Examples include, but are not limited to, glycerin, glucose, honey, lactic acid, polyethylene glycol, propylene glycol, sorbitol, sucrose, and trehalose. See also *CTFA Dictionary* 1773–1774.

What is meant by "buffering agents" is one or more compounds that can maintain a desired pH in an aqueous environment and the buffering agents are used in an amount which produces the desired function provided that the amount does not effect the stability of the solution. Examples include, but are not limited to, boric acid, citric acid, lactic acid, fumaric acid, phosphoric acid, and salts thereof. See also *CTFA Dictionary* 1733–1734.

What is meant by "chelating agents" is one or more compounds that can complex and subsequently inactivate ions in the formulation and the chelating agents are used in an amount which produces the desired function provided that the amount does not effect the stability of the solution. Examples include, citric acid, disodium edetate, pentapotassium triphosphate, and phytic acid. See also *CTFA Dictionary* 1734–1735.

What is meant by "preservatives" is one or more compounds that prevent or reduce or slow down microbial growth and the preservatives are used in an amount which produces the desired function provided that the amount does not effect the stability of the solution. Examples include, but are not limited to, benzoic acid, butylparaben, ethylparaben, propylparaben, methylparaben, sorbic acid, phenoxyethanol, and triclosan. See *CTFA Dictionary* 1765–1766.

pH Adjusters are also present in some embodiments of the invention and the pH Adjusters are used in an amount which produces the desired function provided that the amount does not effect the stability of the solution. "pH adjuster" are acids or bases that can be used to adjust the pH of the finished product to the desired level. Examples include, but are not limited to, acetic acid, ammonia, citric acid, ethanolamine, formic acid, oxalic acid, potassium hydroxide, sodium hydroxide, and triethanolamine. See also Wenniger and McEwen, eds., 2 *International Cosmetic Ingredient Dictionary and Handbook* 1764 (2000 ed.) (hereinafter "CFTA Dictionary"). All cited references in this application are herein incorporated by reference.

Further an embodiment of the invention may include one or more moisturizers, preferably propylene glycol and the moisturizers are used in an amount which produces the desired function provided that the amount does not effect the stability of the solution. Additionally, emulsifying agents may be desirable, preferably Ceteareth-20, manufactured by Promateen Chemicals Inc., which is a polyethylene glycol ether of cetearyl alcohol. Ceteareth-20 has 20 moles of ethylene oxide which is added to the non-ionic surfactant to increase its water solubility. In the event that an emulsion stabilizer is used, the preferred one is a mixture of cetyl and stearyl alcohols, sold by Croda Inc. under the name Cetearyl alcohol.

In order to prevent the degradation caused by oxidation, antioxidants may be included in the formulation and the antioxidants are used in an amount which produces the desired function provided that the amount does not effect the stability of the solution. Antioxidants include, but are not limited to free radical scavengers and reducing agents such as, acetyl cysteine, ascorbic acid, butylated hydroxytoluene, green tea extract, caffeic acid, cysteine, tocopherol, ubiquinone, and propyl gallate, preferably butylated hydroxytoluene ("BHT"). See *CFTA Dictionary* 1727.

What is meant by "hair conditioning agents" or "conditioning agents" are compounds that can alter the texture, appearance, styling, or feel of the hair and the conditioning agents are used in an amount which produces the desired function provided that the amount does not effect the stability of the solution. Examples include, but are not limited to, alanine, arginine, biotin, calcium panthothenate, dimethicone, cyclomethicone, hydrolyzed plant protein, and polyquaterniums, preferably stearalkonium chloride, sold under the name Ammonyx-4 by Stepan Company. See *CFTA Dictionary* 1752–1759.

In other embodiments, in addition to the pediculicides, ovacides and Solvent Matrices, these compositions can further comprise adjuvants and the adjuvants are used in an amount which produces the desired function provided that the amount does not effect the stability of the solution. Examples of adjuvants include, but are not limited to vehicles, stabilizers, moisturizers, cleansing surfactants, emulsifying surfactants, emulsifying stabilizers, foam-boosting surfactants, emollient skin conditioning agents, humectants, hair conditioning agents, buffering agents, pH adjusters, chelating agents, antioxidants, preservatives, botanical extracts, fragrances, and dyes.

In another embodiment, the composition includes one or more pediculicide and ovacide, the Solvent Matrices, and one or more stabilizers to prevent physical separation of the formulation ("Stabilizers"). Non-acrylic decadiene crosspolymers, including but not limited to Stabileze QM and Stabileze 06 (preferably Stabileze QM) manufactured by International Specialty Products may be employed to stabilize and optionally to thicken the formulations. Stabileze QM and Stabileze 06 are benzene-free copolymers of methyl vinyl ether/maleic anhydride crosslinked with 1,9-decadiene. The INCI name for Stabileze 06 and Stabileze QM is PVM/MA Decadiene crosspolymers. Stabileze 06 has a particle size of <850μ. Stabileze QM has a particle size of <75μ. Since Stabileze QM has a smaller particle size, it may be dispersed faster than Stabileze 06 and may be more rapidly converted to a gel. In some embodiments, a neutralizer of the stabilizer may be required to neutralize the formulation to an approximate pH of 5.5 in order to allow thickening of the formulation. A preferred neutralizer is sodium hydroxide.

Stabilizers may also include but are not limited to acrylates/aminoacrylates C10–30 Alkyl PEG-20 Itaconate copolymer, long chain acyl derivatives (including but not limited to ethylene glycol distearate and ethylene glycol monostearate), alkanoamides (including but not limited to cocamide MEA), esters of long chain fatty acids (including but not limited to stearyl stearate), alkyl dimethylamine oxides, methylcellulose, hydroxybutyl methylcellulose, hydroxypropylcellulose, hydroxypropyl methylcellulose, hydroxyethyl cellulose, distearyl phthalic amide (e.g. Stephan SAB-2), di(hydrogenated) tallow phthalic amide (e.g. Stephan TAB-2), primary amines with a fatty alkyl moiety of at least 16 carbons (including but not limited to palmitate amine or stearamine), polyacrylic acids, polysaccharide gums (including but not limited to Xanthan Gum), colloidal clays (including but not limited to benzyl dimethyl hydrogenated tallow ammonium montmorillonite) and colloidal silica.

One of the preferred embodiments is in the form of a conditioner or cream rinse for human hair or animal hair. Hair conditioning agents may be included in the formulation.

The compositions can be administered topically to an animal, by the direct laying on or spreading of the composition on the skin or hair, preferably of a mammal, most preferably of a human. The compositions useful in the subject invention involve formulations suitable for topical application to mammalian skin or hair. Additionally, the compositions may be made into a wide variety of product types. These include, but are not limited to solutions, aerosols, lotions, creams, gels, sticks, ointments, pastes, cream rinses, shampoos, and body washes. The preferred embodiments are cream rinses, conditioners and shampoos.

Vehicles include but are not limited to water, propylene glycol, butylene glycol, ethanol, isopropanol, silicones. Preferably, the vehicle is water.

The invention will be clarified further by a consideration of the following examples.

EXAMPLE 1

Testing of Spinosyn A and Spinosyn D on *Pediculis Captitis* Eggs

Both Spinosyn A and Spinosyn D are sold together as the active ingredient for Conserve SC. Conserve SC is a commercial product from DowElanco used for insect control of turf and ornamental plants. The combination of Spinosyn A and Spinosyn D is known as Spinosad. Conserve SC contains 11.60%, by weight, of the Spinosad. Spinosad contains approximately 80% Spinosyn A and 20% Spinosyn D. Three dilutions of the Conserve SC were created:

Dilution 1 contained 8.62% Conserve SC, 15% isopropanol, 10% propylene carbonate, and 53.45% deionized water. Dilution 1 resulted in a 1% Spinosad concentration.

Dilution 2 contained 21.55% Conserve SC, 15% isopropanol, 10% propylene carbonate, and 66.38% deionized water. Dilution 2 resulted in a 2.5% Spinosad concentration.

Dilution 3 contained 43.10% Conserve SC, 15% isopropanol, 10% propylene carbonate, and 31.9% deionized water. Dilution 3 resulted in a 5% Spinosad concentration.

An in vitro test of Dilutions 1, 2, and 3 was conducted using fresh specimens of *pediculus capitis* eggs. Specimens were collected from volunteers who had abundant nits. Collected eggs were examined for viability. A viable egg is shiny, plump, with an intact operculum, and in more developed eggs, an eye spot. Eggs that were dry, shrunken, indented or otherwise damaged were rejected, as were any eggs containing air pockets.

The ovacidal assay was conducted at ambient room temperature (25° to 35° C.) and humidity (70–90% RH). Ten hairs with viable eggs were sandwiched between small adhesive labels, allowing 2 cm of the hairs to protrude, with the eggs aligned at the distal end. Immediately prior to testing, the dilutions were shaken thoroughly and dispensed into clean glass vials. The eggs were completely immersed in the formulations for ten minutes. Following immersion, the hair and eggs were rinsed in a gentle stream of filtered water from a squeeze bottle to simulate natural shower conditions. They were allowed to air dry for 30 minutes before being placed in capped vials for incubation at 28° to 32° C., RH 70–90%.

Ten batches of ten eggs were tested for each dilution for a total of one hundred eggs for each dilution. One hundred untreated eggs and one hundred eggs immersed in water were used as controls.

Another set of ten batches of ten eggs each (for a total of 100 eggs) were tested on three successive days. After immersion and rinsing, these eggs were allowed to air dry, and then stored in separate, glass vials. The same eggs were tested on three consecutive days and then left to incubate for two weeks.

Ovacidal activity was recorded as number of eggs tested, number of eggs hatched, number of eggs not hatched, and number of eggs stillborn. What was meant by "stillborn" referred to the nymphs that reach maturity, are able to lift the operculum, or cap of the egg, but are unable to fully emerge. These stillborn eggs were considered non-viable.

All three dilutions demonstrated good ovacidal activity. No significant difference in the activity of the dilutions were observed. There was no significant difference between a single treatment of 10 minutes followed by rinsing and a 10-minute treatment on three consecutive days (=3 treatments). The high hatch rates (96% to 98%) of the eggs treated with water in the identical manner as the dilutions indicate that every aspect of the conduct of the test was optimal, including the selection of eggs by the collecting teams, protection of the eggs from heat, lack of contamination by toxic agents on the hands of the collectors and the investigators, and the incubation conditions. Table 1 shows the ovacidal activity for the single 10-minute immersion followed by a water rinse and two week incubation. Table 2 shows the ovacidal activity for 10-minute immersion on three successive days followed by two week incubation.

TABLE 1

| Dilution | # of Eggs Tested | # of Eggs Hatched | # of Eggs Not Hatched | # of Eggs Stillborn | % of Eggs Hatched |
|---|---|---|---|---|---|
| Dilution 1 (1% Spinosad) | 100 | 1 | 96 | 3 | 1% |
| Dilution 2 (2.5% Spinosad) | 100 | 0 | 96 | 4 | 0% |
| Dilution 3 (5% Spinosad) | 100 | 2 | 92 | 6 | 2% |
| Water | 100 | 96 | 4 | 0 | 96% |
| Untreated | 110 | 105 | 5 | 0 | 95% |

TABLE 2

| Dilution | # of Eggs Tested | # of Eggs Hatched | # of Eggs Not Hatched | # of Eggs Stillborn | % of Eggs Hatched |
|---|---|---|---|---|---|
| Dilution 1 (1% Spinosad) | 100 | 0 | 100 | 0 | 0% |

TABLE 2-continued

| Dilution | # of Eggs Tested | # of Eggs Hatched | # of Eggs Not Hatched | # of Eggs Stillborn | % of Eggs Hatched |
|---|---|---|---|---|---|
| Dilution 2 (2.5% Spinosad) | 100 | 0 | 98 | 2 | 0% |
| Dilution 3 (5% Spinosad) | 100 | 0 | 99 | 1 | 0% |
| Water | 100 | 98 | 2 | 0 | 98% |

EXAMPLE 2

In-vitro Ovacidal Testing

In vitro tests were conducted on human head lice with six formulations in order to study the pediculicidal and ovacidal activity of the formulations. No human subjects were used. The ovacidal results were as follows:

TABLE 3

| Description | Active Ingredient % | Single Exposure Ovacidal Rate | Double Exposure Ovacidal Rate |
|---|---|---|---|
| Cream Rinse A | 1% Spinosad | 80% | 100% |
| Cream Rinse A1 | 2% Spinosad | 95% | 100% |
| Cream Rinse B | 1% Spinosad | 85% | 84% |
| Cream Rinse C | 1% Spinosad | 76% | 94% |
| Nix ® (control) | 1% Permethrin | 76% | 58% |
| Deionized Water | | 11% | 8% |

Note that the 76% ovacidal rate for Nix ® after single exposure is an outlier versus the prior testing which was ususally 50–60% ovacidal rate after single exposure.

TABLE 4

| Trade Name | INCI Name | Cream Rinse A | Cream Rinse A1 | Cream Rinse B | Cream Rinse C |
|---|---|---|---|---|---|
| | Deionized Water | 44.8 | 44.25 | 44.82 | 44.81 |
| Stabileze QM | PVM/MA Decadiene Crosspolymer | 1.1 | 1.1 | 1.1 | 1.1 |
| Propylene Glycol | Propylene Glycol | 3 | 3 | 3 | 3 |
| Cetostearyl Alcohol NF | Cetearyl alcohol | 3 | 3 | 3 | 3 |
| Procol-CS-20 | Ceteareth-20 | 0.9 | 0.9 | 0.9 | 0.9 |
| Ammonyx 4 (18%) | Stearalkonium Chloride | 4.17 | 4.17 | 4.17 | 4.17 |
| Benzyl Alcohol | Benzyl Alcohol | 10 | 10 | 10 | 10 |
| Hexylene Glycol | Hexylene Glycol | 6 | 6 | — | — |
| Butylene Glycol | Butylene Glycol | — | — | 5 | — |
| Dipropylene Glycol | Dipropylene Glycol | — | — | — | 5 |
| Hydrolite-5 | Pentylene Glycol | 4 | 4 | 5 | 5 |
| Isopropyl alcohol | Isopropyl alcohol | 20 | 20 | 20 | 20 |
| Spinosad (91.4%) | Spinosyn A & D | 1.095 | 2.19 | 1.095 | 1.095 |
| BHT | Butylated Hydroxytoluene | 0.1 | 0.1 | 0.1 | 0.1 |
| Sodium Hydroxide (10% soln.) | Sodium Hydroxide | 1.83 | 1.29 | 1.81 | 1.82 |
| | | 100 | 100 | 100 | 100 |

In this test, Single Exposure means that the ova were exposed to the formulation for 10 minutes on Day 1, Double Exposure means that the ova were exposed to the formulation for 10 minutes on Day 1 and Day 4. Ovacidal Rate means the percent of louse ova unhatched after a 14 day incubation period.

Therefore, all of the cream rinses effectively deliver Spinosad into the louse ova resulting in strong ovacidal activity. Double exposures of Cream Rinse A and Cream Rinse A1 are most effective with 100% mortality rates of the ova in-vitro, while double exposures of any level of Spinosad increases ovacidal effectiveness. Finally, Spinosad 1% and 2% formulations are superior to Nix®. Nix® is the prior art lice treatment currently marketed to treat lice infestation.

EXAMPLE 3

In-Vitro Pediculicidal Testing

The following are results taken for the same formulations as Example 3 as tested on adult lice for the pediculicidal rates.

TABLE 5

| Formulation | Active Ingredient % | Single Exposure 1-Minute Immersion | | | Single Exposure 10-Minute Immersion | | |
|---|---|---|---|---|---|---|---|
| | | % Dead | % Moribund | % Alive & Well | % Dead | % Moribund | % Alive & Well |
| A2 | 0.5% Spinosad | 77% | 23% | — | 100% | — | — |
| A | 1% Spinosad | 92% | 8% | — | 100% | — | — |
| A1 | 2% Spinosad | 82% | 18% | — | 100% | — | — |
| B | 1% Spinosad | 92% | 8% | — | 97% | 3% | — |
| C | 1% Spinosad | 87% | 13% | — | 100% | — | — |

TABLE 5-continued

| | | Single Exposure 1-Minute Immersion | | | Single Exposure 10-Minute Immersion | | |
|---|---|---|---|---|---|---|---|
| Formulation | Active Ingredient % | % Dead | % Moribund | % Alive & Well | % Dead | % Moribund | % Alive & Well |
| Nix® | 1% Permethrin | 92% | 8% | — | 92% | 8% | — |
| Deionized Water | — | 3% | — | 97% | 2% | — | 98% |

All measurements on this chart were taken at 4 hours after exposure. Moribund means that the lice were in terminal stages of life, from which they can never recover any useful function. In this phase, the lice may show signs of central nervous system or peripheral nerve toxicity, such as tremors, convulsions or twitching of a leg or antenna.

From this study, one can conclude that 0.5%, 1% and 2% Spinosad deliver excellent pediculicidal activity at 1-minute and 10-minute exposure times. Formulations A, A1 and A2 have superior pediculicidal activity to Nix® after a 10-minute immersion time.

TABLE 6

| Trade Name | INCI Name | Cream Rinse A2 | Placebo |
|---|---|---|---|
| | Deionized Water | 45.022 | 46.046 |
| Stabileze QM | PVM/MA Decadiene Crosspolymer | 1.1 | 1.1 |
| Propylene Glycol | Propylene Glycol | 3 | 3 |
| Cetostearyl Alcohol NF | Cetearyl alcohol | 3 | 3 |
| Procol-CS-20 | Ceteareth-20 | 0.9 | 0.9 |
| Ammonyx 4 (18%) | Stearalkonium Chloride | 4.17 | 4.17 |
| Benzyl Alcohol | Benzyl Alcohol | 10 | 10 |
| Hexylene Glycol | Hexylene Glycol | 6 | 6 |
| Butylene Glycol | Butylene Glycol | — | — |
| Dipropylene Glycol | Dipropylene Glycol | — | — |
| Hydrolite-5 | Pentylene Glycol | 4 | 4 |
| Isopropyl alcohol | Isopropyl alcohol | 20 | 20 |
| Spinosad (91.4%) | Spinosyn A & D | 0.548 | — |
| BHT | Butylated Hydroxytoluene | 0.1 | 0.1 |
| Sodium Hydroxide (10% soln.) | Sodium Hydroxide | 2.16 | 1.684 |

Since it is critical that the compositions of this invention are not irritants to human skin, we performed a Draize sensitization study (repeat insult patch test) using a placebo (described in the table above) for one of the vehicles. 100 human subjects were involved for 5 weeks. No subject showed sensitization when the vehicle was applied to the skin.

It is understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A method of controlling adults and ova of the species of order Anoplura by topically applying to one or more of skin and hair a composition comprising:
   a solution of an effective amount of one or more agents, having pediculicidal and ovacidal properties, selected from the group consisting of Spinosad, Spinosyn, Spinosyn A, Spinosyn D and mixtures thereof and;
   one or more stabilizers, wherein the stabilizers comprise polyvinyl methyl ether/maleic anhydride ("PVM/MA") decadiene crosspolymers; and
   wherein the stabilizers have a particle size of <75μ.

2. A method of controlling adults and ova of the species of order Anoplura by topically applying to one or more of skin and hair a composition comprising:
   a solution of an effective amount of one or more agents, having pediculicidal and ovacidal properties, selected from the group consisting of Spinosad, Spinosyn, Spinosyn A, Spinosyn D and mixtures thereof and;
   one or more stabilizers, wherein the stabilizers comprise polyvinyl methyl ether/maleic anhydride ("PVM/MA") decadiene crosspolymers; and
   wherein the solution comprises a solvent consisting of one or more of the following: benzyl alcohol, pentylene glycol, isopropyl alcohol, hexylene glycol, butylene glycol, and dipropylene glycol.

3. A method of controlling adults and ova of the species of order Anoplura by topically applying to one or more of skin and hair a composition comprising:
   a solution of an effective amount of one or more agents, having pediculicidal and ovacidal properties, selected from the group consisting of Spinosad, Spinosyn, Spinosyn A, Spinosyn D and mixtures thereof;
   one or more stabilizers, wherein the stabilizers comprise polyvinyl methyl ether/maleic anhydride ("PVM/MA") decadiene crosspolymers;
   one or more moisturizers;
   one or more emulsion stabilizers;

one or more emulsifying agents;
one or more conditioning agents;
one or more antioxidants; and
one or more pH adjuster.

4. The method of claim 3 wherein the moisturizer comprises propylene glycol.

5. The method of claim 3 wherein the emulsion stabilizer comprises a mixture of cetyl and stearyl alcohols.

6. The method of claim 3 wherein the emulsifying agent comprises Ceteareth-20.

7. The method of claim 3 wherein the conditioning agent comprises stearalkonium chloride.

8. The method of claim 3 wherein the antioxidant comprises butylated hydroxytoluene ("BHT").

9. The method of claim 3 wherein the pH adjuster comprises sodium hydroxide.

10. The method of claim 3 further comprising one or more viscosity increasing agents.

11. The method of claim 10 wherein the viscosity increasing agent comprises a mixture of cetyl and stearyl alcohols.

12. A method of controlling adults and ova of the species of order Anoplura by topically applying to one or more of skin and hair a composition comprising:
- about 44% water;
- about 1.1% PVM/MA decadiene crosspolymer;
- About 3% propylene glycol;
- About 3% cetearyl alcohol;
- About 0.9% ceteareth-20;
- About 4.17% stearalkonium chloride;
- About 10% benzyl alcohol;
- About 6% hexylene glycol;
- About 4% pentylene glycol;
- About 20% isopropyl alcohol;
- About 2.19% mixture of spinosyn A and spinosyn D in an approximate 85:15 weight ratio;
- About 0.1% BHT; and
- 1.29% sodium hydroxide (10% solution).

* * * * *

UNITED STATES PATENT AND TRADEMARK OFFICE
CERTIFICATE OF CORRECTION

PATENT NO. : 7,030,095 B2  Page 1 of 1
APPLICATION NO. : 10/230460
DATED : April 18, 2006
INVENTOR(S) : Herwig Janssen et al.

It is certified that error appears in the above-identified patent and that said Letters Patent is hereby corrected as shown below:

u.s. Pat. Doc.
In References Cited on the face of the patent, the following references should be added --5,653,970 8/1997 Vermeer-- and --WO 00/01347 1/2000-- This is a clerical error by the PTO.

In Column 10, line 25, "filly" should read as --fully-- This is a typographical error by the PTO.

Signed and Sealed this

Twenty-second Day of August, 2006

JON W. DUDAS
*Director of the United States Patent and Trademark Office*